United States Patent
Sotoyama et al.

(10) Patent No.: US 7,427,499 B2
(45) Date of Patent: Sep. 23, 2008

(54) BIFIDOBACTERIUM LONGUM

(75) Inventors: Kazuyoshi Sotoyama, Kanagawa-ken (JP); Akinori Hiramatsu, Kanagawa-ken (JP); Jin-zhong Xiao, Kanagawa-ken (JP); Noritoshi Takahashi, Kanagawa-ken (JP); Shizuki Kondo, Kanagawa-ken (JP); Tomoko Yaeshima, Kanagawa-ken (JP); Sachiko Takahashi, Kanagawa-ken (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 671 days.

(21) Appl. No.: 10/709,674

(22) Filed: May 21, 2004

(65) Prior Publication Data

US 2004/0202749 A1    Oct. 14, 2004

Related U.S. Application Data

(63) Continuation of application No. PCT/JP02/12162, filed on Nov. 21, 2002.

(30) Foreign Application Priority Data

Dec. 7, 2001 (JP) .............................. 2001-374327

(51) Int. Cl.
*C12N 1/20* (2006.01)
(52) U.S. Cl. .................... 435/252.1; 424/93.4
(58) Field of Classification Search ............... None
See application file for complete search history.

(56) References Cited

U.S. PATENT DOCUMENTS 5,711,977 A * 1/1998 Yang et al. .................... 426/61
6,306,638 B1  10/2001 Yang et al. ................. 435/252.1

FOREIGN PATENT DOCUMENTS

| JP | 52-83974 | 7/1977 |
| JP | 58-224685 | 12/1983 |
| JP | 04-320642 | 11/1992 |
| JP | 09-322762 | 12/1997 |
| JP | 11-075830 | 3/1999 |
| WO | WO 00/42168 | 7/2000 |

OTHER PUBLICATIONS

European Patent Office, *Supplementary European Search Report and Date Stamped Letter*, dated Nov. 24, 2004 (4 pages).
J. H. Martin and K. M. Chou, *Selection of Bifidobacteria for Use as Dietary Adjuncts in Cultured Dairy Foods: I—Tolerance to pH of Yogurt1*, Cultured Dairy Products Journal, Nov. 1992, pp. 21-26.
ISA/JP, *International Search Report*, Feb. 18, 2003 (7 pages).
Takatoshi Itoh, *Functional Benefits from Lactic Acid Bacteria used in Cultured Milk*, Nicchiku Kaihou, 1992, vol. 63, No. 12, pp. 1276-1289.
Rinsho Kensa, *Briggs agar*, Tomotari Mitsuoka, 1974, vol. 18, No. 11, pp. 1163-1172.
Chonaikin no sekai, *A Color Atlas of Anaerobic Bacteria*, Tomotari Mitsuoka, 1980, published by Soubunsha, pp. 319 and 322.

* cited by examiner

*Primary Examiner*—Irene Marx
(74) *Attorney, Agent, or Firm*—Wood, Herron & Evans, L.L.P.

(57) ABSTRACT

17It is intended to provide *Bifidobacterium longum* having the following bacteriological properties and microbial powders, foods and beverages containing this *Bifidobacterium longum*: (1) having such fermentation ability as to make a milk base medium to pH 4.6 or below; (2) showing a survival rate of 50% or more in the case of, after attaining pH 4.4 to 4.6 in a milk base medium, quenching and storing at 10° C. for two weeks; and (3) having such gastric juice tolerance as to yield a survival rate of 10% or more in the case of storing in artificial gastric juice (pH 3.0) at 37° C. for two hours.

1 Claim, No Drawings

BIFIDOBACTERIUM LONGUM

This application is a continuation of PCT/JP02/12162, filed Nov. 21, 2002, which claims the priority of Japanese Patent No. 2001-374327,filed Dec. 7, 2001, the disclosures of which are hereby incorporated herein by reference in their entireties.

TECHNICAL FIELD

The present invention relates to novel *Bifidobacterium longum* which has excellent fermentation characteristic, preservability under acidic conditions and during distribution, and tolerance to gastric juice, and which readily exerts physiological functions.

Also, the present invention relates to novel *Bifidobacterium longum* powders, foods, and beverages containing the above *Bifidobacterium longum*.

BACKGROUND ART

Strains of *Bifidobacterium*, such as *Bifidobacterium longum* (hereinafter referred to as *bifidus* bacteria), are some of the predominant bacteria of intestinal microflora which may be formed in the intestinal tract of humans, and it is known that consumption of the bacteria is effective for improving the intestinal environment. Recently, demands for food containing *bifidus* bacteria has increased, and *bifidus* bacteria have been widely used in cultured milk, acidophilus milk, and so forth. Also, various reports have been made on the bioactivity of the *bifidus* bacteria, such as antitumor activity, and attempts have been made to utilize the bioactivity for various health foods. As described above, while it is anticipated that *bifidus* bacteria is effective for, for example, maintenance of the intestinal microflora and improvement thereof, it is necessary to continuously consume the *bifidus* bacteria to make the *bifidus* bacteria exert their effect.

However, the *bifidus* bacteria do not grow well on a milk base medium, and it takes a long period of time for the pH and the number of bacteria to reach a certain value. Also, since it is difficult to preserve the *bifidus* bacteria under acidic conditions and the bacteria easily die, it is a significant problem to maintain the number of the bacteria during distribution.

On the other hand, although it is said that living *bifidus* bacteria have the most effective bioactivity, various factors killing or inhibiting the growth of lactic acid bacteria and *bifidus* bacteria exist in the digestive tracts of humans. In particular, these bacteria must survive low pH of gastric juice and digestive enzymes when it reaches the stomach which is the first hurdle of the digestive tract. Although it depends on the contents, etc., in the stomach, one of the general references of the gastric juice tolerance is to survive for two hours at pH 3.0 (Itoh et al., Nicchiku Kaihou, Vol. 63, No. 12, pp. 1276-1289, (1992)).

However, most of the *bifidus* bacteria are weak at low pH, and it is said that the probability that one will pass through the gastric juice is lower than for *lactobacilli*, etc.

Accordingly, it is desired, in terms of developing foods and beverages containing the *bifidus* bacteria, to develop *bifidus* bacteria which is capable of growing to a certain number in a short period of time (i.e., fermentation characteristic), maintaining more than a certain number of living bacteria during distribution after its production or during consumption (i.e., acid tolerance), and exerting bioactivity by reaching the digestive tract (intestinal tract, in particular) alive using its gastric acid resistance.

From the viewpoints mentioned above, studies have been made on the fermentation characteristic, acid resistivity, and gastric acid resistivity of the *bifidus* bacteria. For example, it is known that a variant of *Bifidobacterium bifidum* exists which has acid tolerance and fermentation characteristics in a milk base medium (Japanese Examined Patent Application, Second Publication No. Sho 56-42250). Also, it is known that a strain of *Bifidobacterium longum* has acid tolerance (Japanese Examined Patent Application, Second Publication No. Sho 59-53829 (hereinafter referred to as the cited document 1) and Japanese Unexamined Patent Application, First Publication No. Hei 11-75830). Moreover, it is known that *Bifidobacterium breve* grow in a reconstituted skim milk medium and has acid tolerance (Japanese Unexamined Patent Application, First Publication No. Hei 4-320642).

However, it takes more than fifteen hours for the above-mentioned *Bifidobacterium bifidum* and *Bifidobacterium breve* to ferment the milk base medium to a certain pH. Also, the survival rate of many of the acid resistant strains, when stored in an acidic milk product or fruit juice (pH 4.0-4.8) in a refrigerator, is not satisfactory. That is, the acid tolerance of the above-mentioned bacterial strains is not sufficient. Also, although there is a report (Japanese Unexamined Patent Application, First Publication No. Hei 9-322762 (hereinafter referred to as the cited document 2) on a mutant strain of the *Bifidobacterium longum* having a strong gastric juice tolerance which is said to be related to the survival rate in a digestive tract (intestinal tract), the preservability of the mutant strain is not sufficient, as is also obvious from the results of tests which will be described later.

Accordingly, it is an object of the present invention to provide *bifidus* bacteria having excellent growth rate in a milk base medium, and acid tolerance, and whose number can be readily maintained to be more than a certain number in a cultured milk product and during circulation. The bacteria also has a strong gastric juice tolerance, and exerts bioactivity by reaching the digestive (intestinal tract) alive.

Also, it is an object of the present invention to provide powders, foods and beverages containing the *bifidus* bacteria.

DISCLOSURE OF INVENTION

The inventors of the present invention, after carrying out diligent research to achieve the above objects, found that *Bifidobacterium longum* having: (1) fermentation characteristic as to yield a milk base medium to pH 4.6 or lower; (2) survival rate of 50% or higher, after attaining a pH 4.4 to 4.6 in a milk base medium, quenching and storing at 10° C. for two weeks; and (3) gastric juice tolerance as giving a survival rate of 10% or higher in the case of storing in artificial gastric juice of pH 3.0 at 37° C. for two hours, can be grown so that the number of cells becomes more than a certain number in a short period of time, a certain number of living cells can be maintained during distribution and consumption after its production, and the bacteria is capable of exerting bioactivity by reaching the digestive tract (an intestinal tract, in particular) alive using its gastric juice tolerance, and have completed the present invention.

That is, the present invention provides *Bifidobacterium longum* having the following bacteriological characteristics:

(1) fermentation characteristics so as to make a milk base medium to pH 4.6 or lower;

(2) survival rate of 50% or higher, after attaining pH 4.4 to 4.6 in a milk medium, quenching and storing at 10° C. for two weeks; and (3) gastric juice tolerance as giving a survival rate of 10% or higher in the case of storing in artificial gastric juice of pH 3.0 at 37° C. for two hours.

The present invention also provides powders containing the above-mentioned *Bifidobacterium longum*.

The present invention also provides foods and beverages containing the above-mentioned *Bifidobacterium longum*.

BEST MODE FOR CARRYING OUT THE INVENTION

*Bifidobacterium longum* according to the present invention possesses the above mentioned characteristics of (1), (2), and (3).

(1) relates to fermentative characteristics. In general, *bifidus* bacteria do not grow well in a milk base medium, and it takes a long period of time to reach a certain pH and number of cells. If a strain of bacteria having strong fermentation ability to make the pH of a milk base medium to 4.6 or lower is used, it becomes possible to complete the fermentation in a short period of time, and a certain number of bacterial cells (for example, ten million cells per 1 ml of cultured milk product) can be readily maintained in a food or beverage using the bacteria (for example, acidic dairy products, such as cultured milk products, and fruit juice products), and hence the product efficiency can increase.

(2) relates to acid tolerance by which a certain number of bacterial cells can be maintained in a stored cultured milk product using *bifidus* bacteria or during distribution. In general, the pH of a cultured milk product or a fruit juice product is 4.0-4.8, and a sell-by date thereof is generally about two weeks under storing conditions of 10° C. or lower. The inventors of the present invention found that bacteria whose survival rate is 50% or higher when rapidly cooled down to 10° C. after the pH of a milk base medium reaches 4.4-4.6 and stored for two weeks, has a strong acid tolerance and a certain number of living cells can be maintained in a cultured milk product, etc., within a sell-by date period. On the other hand, bacteria whose survival rate is 5% or lower when stored in a citrate or malate buffered solution of pH 4 at 10° C. for four days, for example, cannot be said to have sufficient acid tolerance. Note that a milk base medium means a medium containing milk components, such as milk, dairy cream, butter, and skim milk, and including 3% or more of milk protein.

(3) relates to a gastric juice tolerance necessary for *bifidus* bacteria to reach a digestive (intestinal) tract alive. *Bifidus* bacteria exerts bioactive functions when reaching an intestinal tract after being taken orally and passing through the stomach. However, since the pH of the stomach is low, most of cells are killed in the stomach, and only a few manage to reach the intestinal tract. If the survival rate when maintained in an artificial gastric juice of pH 3.0 at 37° C. for two hours is 10% or higher, it is considered that the gastric juice tolerance of the bacteria is high, and many of the cells can reach an intestinal tract alive.

By taking *Bifidobacterium longum* having the above-mentioned bacteriological characteristics of (1)-(3), many of the cells can reach an intestinal tract alive, and the bioactive function as *bifidus* bacteria is readily exerted.

*Bifidobacterium longum* according to the present invention can be obtained, for example, by using the following method. First, strains of bacteria are separated from various samples, and cells having excellent fermentation characteristic on a milk base medium, i.e., having fermentative characteristics capable of making pH of the milk base medium to be 4.6 or lower, is selected. Then, a cultured milk product is prepared using the selected strain as a starter, and strains having excellent survival rate when stored at a low temperature, i.e., one whose survival rate is 50% or higher, after attaining pH 4.4 to 4.6 in a milk medium, quenching and storing at 10° C. for two weeks. Thereafter, the strain is stored in artificial gastric juice of pH 3.0 at 37° C. for two weeks, and a strain having excellent gastric juice tolerance which shows survival rate of 10% or higher is selected to obtain the strain of the present invention.

This will be explained further in detail.

1. Acquisition of Strain

The inventors of the present invention, to obtain the strain of bacteria having the above-mentioned characteristics in nature, diluted samples obtained from natural habitats using an anaerobic dilution buffer ("Chonaikin no sekai", Tomotari Mitsuoka, pp. 322, published by Soubunsha, 1980, hereinafter referred to as the reference 1), applied it onto a BL agar medium flat plate (the reference 1, pp. 319), and incubated it anaerobically at 37° C. Then, among the colonies obtained, strains which showed morphological characteristics of *bifidobacteria* and were Gram positive of rod, club or Y-shaped cell appearance under microscopic observation of applied specimens were collected and streaked onto a BL agar flat plate to repeat anaerobic incubation using the same method described above. In this manner, pure isolated strains were obtained. Then, tests for fermentation and survival rate during conservation of the strains were conducted using the following methods, and about twenty strains having excellent results were obtained. After this, a test for gastric juice tolerance was performed, and strains which showed excellent survival rate in artificial gastric juice of pH 3.0 were obtained. Among them, a strain which was most excellent was deposited under the Budapest Treaty on the International Recognition of the Deposit of Microorganisms for the Purposes of Patent Procedure to the International Patent Organism Depository, National Institute of Advanced Industrial Science and Technology (AIST), located at AIST Tsukuba Central 6, 1-1, Higashi, 1-Chome Tsukuba-shi Ibaraki-ken 305-8566. The deposit was made on Oct. 31, 2001 and the strain was given accession number FERM BP-7787. The taxonomic description of the *Bifidobacterium longum* strain is shown below.

2. Bacteriological Characteristics (1) Shape of cell (anaerobically incubated on BL agar medium at 37° C. for 72 hours and observed under a light microscope)

Size: 0.3-0.8 μm×4-10 mμ

Shape: rod (club-shaped or Y-shaped)

(2) Gram staining: positive (3) Colony morphology (when anaerobically incubated on BL agar medium at 37° C. for 72 hours)

Shape: protruded to be circular, convex-pulvinate

Edge: entire

Size: 1-4 mm

Color: dark brown at periphery, charcoal brown at center

Surface: smooth (4) Endspore formation: negative (5) Gas generation: none (6) Motility: none (7) Catalase activity: negative (8) Molar ratio of acetic acid/L(+) lactic acid: 1.5 or larger (9) Fermentation of sugars, carried out using API 50CH system (Japan Biomelue Co.) and a sugar fermentation media of Mitsuoka (refer to the above reference 1, pp. 323)

Positive for L-arabinose, D-xylose, galactose, D-glucose, D-fructose, D-mannose, maltose, lactose, melibiose, sucrose, melezitose, raffinose, and D-turanose; and delayed reaction for α-methyl-D-glucoside: and Negative for glycerol, erythritol, D-arabinose, ribose, L-xylose, adonite, methyl-xyloside, L-sorbose, rhamnose, dulcitol, inositol, mannitol, sorbitol, α-methyl-mannoside, N-acetyl-glucosamin, amygdalin, arbutin, esculin, salicin, cellobiose, trehalose, inulin, starch, glycogen, xylitol, gentiobiose, D-lyxose, D-tagatose, D-fucose, L-fucose, D-arabitol, L-arabitol, gluconate, 2 keto-gluconate, and 5-keto-gluconate.

(10) DNA Homology

Chromosomal DNA of each of *Bifidobacterium longum* ATCC 15707$^T$ and *Bifidobacterium animalis* R101-8$^T$ (available as JCM1190$^T$ in microorganism strain preservation facility of the Institute of Physical and Chemical Research) was extracted and hybridized with chromosomal DNA extracted from *Bifidobacterium longum* FERM BP-7787 using microplate hybridization. The chromosomal DNA extracted from *Bifidobacterium longum* FERM BP-7787 showed 95% homology with the chromosomal DNA extracted from *Bifidobacterium longum* ATCC 15707 while the homology with *Bifidobacterium animalis* R101-8$^T$ was 22%.

As explained above, since *Bifidobacterium longum* FERM BP-7787 of the present invention matches the *bifidus* bacteria shown in the classification reference of the Bergeys Manual of Systematic Bacteriology, Vol. 2, 1986, and from the results of the fermentation characteristic, property, and DNA homology, it is identified as *Bifidobacterium longum*.

3. Fermentation on a Milk Base Medium

Reconstituted skim milk powder medium (11%) including 0.2% yeast extract (a product of Difco Co.) was pasteurized at 115° C. for 15 minutes, and a starter of *Bifidobacterium longum* FERM BP-7787, which was subcultured twice on the same medium, and comparative strains (strains shown in Table 1 other than the strain of the present invention) was inoculated (5%) and incubated at 37° C. for six hours. The number of cells and pH of the incubation liquid were measured. The cell count was conducted using a reinforced clostridial agar (RCA, a product of Oxoid Co.) flat plate. Under the above incubation conditions, *Bifidobacterium longum* FERM BP-7787 was capable of solidifying the milk base medium in a shorter period of time as compared with the comparative strains, and the highest number of *bifidus* bacteria was contained in the medium (Table 1).

TABLE 1

Fermentative characteristics of each strain on milk base medium

| Strain | pH | CFU/ml |
|---|---|---|
| *Bifidobacterium longum* FERM BP-7787 (strain of present invention) | 4.56 | $2.1 \times 10^9$ |
| *Bifidobacterium longum* FERM P-6548 | 5.02 | $7.3 \times 10^8$ |
| *Bifidobacterium longum* ATCC15707 | 5.88 | $1.9 \times 10^8$ |
| *Bifidobacterium longum* ATCC15708 | 5.82 | $9.3 \times 10^7$ |
| *Bifidobacterium longum* ATCC55817 | 5.64 | $4.7 \times 10^8$ |

*Bifidobacterium longum* FERM P-6548: strain described in the cited document 1
*Bifidobacterium longum* ATCC55817: strain described in the cited document 2

4. Acid Tolerance (1) Solitary Fermentation (Reconstituted skim milk powder medium (11%) including 0.2% yeast extract (a product of Difco Co.) was placed in a glass tube and pasteurized at 115° C. for 15 minutes, and a starter of *Bifidobacterium longum* FERM BP-7787 and comparative strains (strains shown in Table 2 other than the strain of the present invention) was inoculated (5%) and incubated at 37° C. until the pH became 4.3-4.4. After this, these were rapidly cooled, and storing tests were conducted at 10° C. The number of cells immediately after the cooling, after one week of storing, and after two weeks of storing was measured using a RCA agar flat plate, and the survival rate at each storing period was calculated.

As a result, most of *Bifidobacterium longum* FERM BP-7787 survived after two weeks of storing at 10° C. on the fermented medium of pH 4.4 showing they have very high survival rate which is superior to that of *Bifidobacterium longum* FERM P-6548 comparative strain (Table 2). Most of *Bifidobacterium longum* ATCC55817, which is known as having gastric juice tolerance, and the other comparative strains could not survive after two weeks of storing.

TABLE 2

Survival rate of each strain on milk base medium

Immediately after cooling

| Strain | Fermentation (hour) | pH | No./ml |
|---|---|---|---|
| *Bifidobacterium longum* FERM BP-7787 (strain of present invention) | 7.0 | 4.40 | $1.8 \times 10^9$ |
| *Bifidobacterium longum* FERM P-6548 | 14.0 | 4.44 | $1.5 \times 10^9$ |
| *Bifidobacterium longum* ATCC15707 | 14.5 | 4.42 | $2.2 \times 10^9$ |
| *Bifidobacterium longum* ATCC15708 | 14.0 | 4.41 | $1.0 \times 10^9$ |
| *Bifidobacterium longum* ATCC55817 | 14.0 | 4.38 | $1.9 \times 10^9$ |

After storing for one week

| Strain | pH | No./ml | Survival rate (%) |
|---|---|---|---|
| *Bifidobacterium longum* FERM BP-7787 (strain of present invention) | 4.31 | $1.9 \times 10^9$ | 105.5 |
| *Bifidobacterium longum* FERM P-6548 | 4.38 | $1.2 \times 10^9$ | 80.4 |
| *Bifidobacterium longum* ATCC15707 | 4.37 | $6.0 \times 10^7$ | 1.8 |
| *Bifidobacterium longum* ATCC15708 | 4.40 | $1.0 \times 10^8$ | 10.1 |
| *Bifidobacterium longum* ATCC55817 | 4.35 | $7.0 \times 10^7$ | 2.8 |

After storing for two weeks

| Strain | pH | No./ml | Survival rate (%) |
|---|---|---|---|
| *Bifidobacterium longum* FERM BP-7787 (strain of present invention) | 4.30 | $1.7 \times 10^9$ | 92.1 |
| *Bifidobacterium longum* FERM P-6548 | 4.35 | $7.5 \times 10^8$ | 50.1 |
| *Bifidobacterium longum* ATCC15707 | 4.33 | $2.0 \times 10^7$ | 0.56 |
| *Bifidobacterium longum* ATCC15708 | 4.40 | $6.0 \times 10^5$ | 0.06 |
| *Bifidobacterium longum* ATCC55817 | 4.34 | $1.5 \times 10^5$ | 0.01 |

*Bifidobacterium longum* FERM P-6548: strain described in the cited document 1
*Bifidobacterium longum* ATCC55817: strain described in the cited document 2

(2) Mixed Fermentation

Raw milk base including 3.0% (W/W) butterfat and 9% (W/W) nonfat milk solid content, which are the same composition as in one used in Example 1 described later, was heated to 70° C., homogenized at a pressure of 15 MPa, pasteurized at 90° C. for 10 minutes, and cooled to 40° C. Mixed culture of *Streptococcus thermophilus* and *Lactobacillus delbrueckii* subsp. *bulgaricus* (0.6%), which was prepared using the same method as in Example 1, was inoculated to the pasteurized base. Also, a starter of *Bifidobacterium longum* FERM BP-7787 and comparative strains (strains shown in Table 3 other than the strain of the present invention), which were cultured at 37° C. using the above mentioned 11% reconstituted skim milk powder medium including 0.2% yeast extract (a product of Difco Co.) until the pH became 4.3-4.4, were inoculated (5%), placed in test tubes, incubated at 37° C. for five hours, and rapidly cooled to conduct storing tests at 10° C. The number of cells immediately after the cooling, after one week of storing, and after two weeks of storing was measured using an RCA agar flat plate, and the survival rate for each storing period was calculated. More than 50% of *Bifidobacterium longum* FERM BP-7787 survived after two weeks of storing at 10° C. on the fermented medium of pH 4.6 or less showing they have acid tolerance superior to that of *Bifidobacterium longum* ATCC55817, which is known as having gastric juice tolerance, and the other comparative strains (Table 3).

TABLE 3

Survival rate of each strain on milk base medium

| Strain | Immediately after cooling | | After storing for one week | | |
|---|---|---|---|---|---|
| | pH | No./ml | pH | No./ml | Survival rate (%) |
| *Bifidobacterium longum* FERM BP-7787 (strain of present invention) | 4.59 | $3.3 \times 10^8$ | 4.20 | $2.5 \times 10^8$ | 75.8 |
| *Bifidobacterium longum* FERM P-6548 | 4.57 | $2.5 \times 10^8$ | 4.23 | $8.0 \times 10^7$ | 32.1 |
| *Bifidobacterium longum* ATCC15707 | 4.60 | $2.1 \times 10^8$ | 4.26 | $2.5 \times 10^6$ | 1.20 |
| *Bifidobacterium longum* ATCC15708 | 4.63 | $1.7 \times 10^8$ | 4.27 | $<1.0 \times 10^4$ | <0.01 |
| *Bifidobacterium longum* ATCC55817 | 4.54 | $2.2 \times 10^8$ | 4.28 | $7.1 \times 10^6$ | 3.20 |

| Strain | After storing for two weeks | | |
|---|---|---|---|
| | pH | No./ml | Survival rate (%) |
| *Bifidobacterium longum* FERM BP-7787 (strain of present invention) | 4.18 | $1.7 \times 10^8$ | 51.5 |
| *Bifidobacterium longum* FERM P-6548 | 4.18 | $7.5 \times 10^7$ | 30.0 |
| *Bifidobacterium longum* ATCC15707 | 4.17 | $2.0 \times 10^3$ | <0.001 |
| *Bifidobacterium longum* ATCC15708 | 4.18 | $<1.0 \times 10^3$ | <0.001 |
| *Bifidobacterium longum* ATCC55817 | 4.16 | $<1.0 \times 10^3$ | <0.001 |

*Bifidobacterium longum* FERM P-6548: strain described in the cited document 1
*Bifidobacterium longum* ATCC55817: strain described in the cited document 2

5. Gastric Juice Tolerance

Tests for gastric juice tolerance were conducted as follows. That is, bacterial cell suspension (0.1 ml) of *Bifidobacterium longum* FERM BP-7787 and that of comparative strains, which were twice activation cultured (37° C., 24 hours) using Briggs liver broth (Rinsho Kensa, Tomotari Mitsuoka, Vol. 18, pp.1163-1172, 1974) and washed once with physiological saline, was added to 9.9 ml of artificial gastric juice (0.2% NaCl, 0.35% pepsin (1:5000) were dissolved in purified water), whose pH was adjusted to 3.0 using filter-sterilized 1M hydrochloric acid. After two hours of contact at 37° C., 1 ml portion thereof was added to 9 ml of phosphate buffer solution (pH 6.5, 67 mM) to stop the process. Then, the number of cells initially present and after the contact was measured using an RCA agar flat plate, and the survival rate was calculated. In this manner, FERM BP-7787 of the present invention showed high gastric juice tolerance which was the same level as that of ATCC55817, while the other strains including FERM P-6548 which has a relatively high acid tolerance, showed almost no tolerance (Table 4).

TABLE 4

Artificial gastric juice tolerance of each strain

| Strain | Initial cell number (CFU/ml) | Survival rate after 2 hour treatment |
|---|---|---|
| *Bifidobacterium longum* FERM BP-7787 (strain of present invention) | $5.1 \times 10^8$ | 23.5 |
| *Bifidobacterium longum* FERM P-6548 | $2.5 \times 10^8$ | 0.01 |
| *Bifidobacterium longum* ATCC15707 | $4.1 \times 10^8$ | 0.01 |
| *Bifidobacterium longum* ATCC15708 | $1.1 \times 10^8$ | <0.001 |
| *Bifidobacterium longum* ATCC55817 | $2.8 \times 10^8$ | 21.3 |

*Bifidobacterium longum* FERM P-6548: strain described in the cited document 1
*Bifidobacterium longum* ATCC55817: strain described in the cited document 2

As described above, since *Bifidobacterium longum* FERM BP-7787 strain of the present invention has strong fermentation characteristics on a milk base medium, excellent survival rate when stored under acidic conditions, and strong tolerance to artificial gastric juice, it is obvious that it has characteristics not possessed by the reference strains of *Bifidobacterium longum* or know bacteria strains. On the other hand, the fermentative characteristics on a milk base medium, and the survival rate when stored in an acidic condition of ATCC 55817 strain, which is known to have gastric acid tolerance, were very inferior and significantly lower as compared with that of FERM BP-7787 of the present invention.

*Bifidobacterium longum* of the present invention is one which is selected from *Bifidobacterium longum* present in nature having fermentation characteristics, acid tolerance, and gastric acid tolerance. Accordingly, *Bifidobacterium longum* of the present invention can be rapidly incubated in a short period of time, and the degree of decrease in the number of living cells in a cultured substance or during storing of a processed product thereof is low. Accordingly, it can be applied to food and drink over a wide pH range.

In addition, since it is confirmed by tests that the survival rate of *Bifidobacterium longum* of the present invention when frozen or freeze-dried is also good, it can be utilized in the form of powder. Moreover, since *Bifidobacterium longum* of the present invention has gastric acid tolerance, and hence can reach a digestive (intestinal) tract alive with high percentage to exert biological function when taken by human or animal, it is extremely effective industrially. For example, it can be not only used as an intestinal function controlling compound for human or animals known for many years, but may also added or mixed with powdered food or feed, or liquid or semi-solid feed or food.

Hereinafter, the present invention will be described further in detail with Examples.

EXAMPLE 1

*Bifidobacterium longum* FERM BP-7787 strain of the present invention was inoculated onto a medium (1000 ml)

including 0.2% (W/W) yeast extract and 11% (W/W) skim milk powder, which was pasteurized at 90° C. for three hours, and incubated for six hours at 37° C. On the other hand, mixed culture (50 ml) of *Streptococcus thermophilus* (Chr. Hansen) and *Lactobacillus delbrueckii* subsp. *bulgaricus* (Chr. Hansen) was inoculated to 10% (W/W) reconstituted skim milk medium (1500 ml) which was pasteurized for 30 minutes at 90° C., and incubated for five hours at 42° C.

Apart from that, raw milk (50 L) including 3.0% (W/W) butterfat and 9% (W/W) nonfat milk solid content was heated to 70° C., homogenized at a pressure of 15 MPa, pasteurized at 90° C. for 10 minutes, and cooled to 40° C. A culture (750 ml) of *Bifidobacterium longum* FERM BP-7787 strain of the present invention, which was pre-incubated as described above, and the mixed culture (300 ml) of *Streptococcus thermophilus* and *Lactobacillus delbrueckii* subsp. *bulgaricus* were inoculated to the sterilized base, filled in a container of 500 ml, sealed, incubated for five hours at 37° C., and rapidly cooled. Lactic acidity and pH of the obtained cultured milk were 0.81% and 4.55, respectively, and $2.3 \times 10^8$/ml of *Bifidobacterium longum* FERM BP-7787 strain, $6.8 \times 10^8$/ml of *Streptococcus thermophilus*, and $3.4 \times 10^7$/ml of *Lactobacillus delbrueckii* subsp. *bulgaricus* were contained therein. The number of cells of *Bifidobacterium longum* FERM BP-7787 contained in the cultured milk after storing for fourteen days at 10° C. was $1.5 \times 10^8$/ml giving the survival rate of 65%.

EXAMPLE 2

A seed culture (500 ml) of *Bifidobacterium longum* FERM BP-7787 strain of the present invention which was pre-incubated for sixteen hours at 37° C. on a medium containing 50 gram of meat extract, 100 gram of peptone, 200 gram of milk sugar, 50 gram of $K_2HPO_4$, 10 gram of $KH_2PO_4$, 4 grams of cystine, and 9.5L of water, was inoculated to the above medium (10L) and incubated for sixteen hours at 37° C. Also, an entire amount of the above medium (10.5L) was inoculated to a medium (200L) having the same composition as the above-mentioned medium and pasteurized for 30 minutes at 90° C., and incubated for sixteen hours at 37° C. The number of living cells after incubation was $3.0 \times 10^9$/ml.

Then, bacterial cells were collected using a sharpless type centrifugal device (15,000 rpm), suspended again in physiological saline of the same amount as the medium which was pasteurized for 30 minutes at 90° C., and collected again using the same centrifugal device. The obtained cells were suspended in a solution (20 L, pasteurized for 30 minutes at 90° C.) including 10% (W/W) skim milk powder, 1% (W/W) sucrose, and 1% (W/W) monosodium glutamate, and freeze-dried using a conventional method. As a result, about 2.2 kg of powder including the bacteria of the present invention was obtained.

EXAMPLE 3

Powder (20 g) including *Bifidobacterium longum* FERM BP-7787 strain of the present invention obtained in Example 2 was added to dry-sterilized starch (14 kg) and milk sugar (6 kg) and uniformly mixed to obtain about 20 kg of intestinal function controlling compound powder including $1.0 \times 10^8$/g of the strain according to the present invention.

EXAMPLE 4

*Bifidobacterium longum* FERM BP-7787 strain of the present invention was inoculated onto a medium (1000 ml) including 0.2% (W/W) yeast extract and 11% (W/W) skim milk powder, which was pasteurized at 90° C. for three hours, and incubated for six hours at 37° C. On the other hand, culture (30 ml) of *Streptococcus cremoris* (Chr. Hansen) was inoculated to 10% (W/W) reconstituted skim milk medium (1000 ml) including 0.6% (W/W) yeast extract, which was pasteurized for 30 minutes at 90° C., and incubated for 16 hours at 30° C.

Apart from that, raw milk (50 L) including 0.5% (W/W) butterfat, 9% (W/W) nonfat milk solid content, and 6.5% sucrose was heated to 70° C., homogenized at a pressure of 15 MPa, pasteurized at 90° C. for 10 minutes, and cooled to 33° C. A culture (750 ml) of *Bifidobacterium longum* FERM BP-7787 strain of the present invention, which was pre-incubated as described above, and the culture (500 ml) of *Streptococcus cremoris* were inoculated to the sterilized base, incubated for 16 hours at 30° C., and rapidly cooled with stirring. The cooled cultured milk was subjected to a homogenizing process of 15 MPa pressure, filled in a container of 200 ml, and sealed to obtain a yoghurt drink.

Lactic acidity and pH of the obtained cultured milk were 0.81% and 4.55, respectively, and $1.5 \times 10^8$/ml of *Bifidobacterium longum* FERM BP-7787 strain, and $9.8 \times 10^8$/ml of *Streptococcus cremoris* were contained therein. The number of cells of *Bifidobacterium longum* FERM BP-7787 strain contained in the cultured milk after storing for 14 days at 10° C. was $8.5 \times 10^7$/ml giving a survival rate of 57%.

*Bifidobacterium longum* according to the present invention has excellent fermentation characteristics and survival rate on a milk base medium, and tolerance to artificial gastric juice. Accordingly, it is possible to rapidly prepare the culture of the strain according to the present invention, and the degree of decrease in the number of living cells in the culture or a product when stored thereof is low. Accordingly, the strain can be applied to foods and beverages of wide pH range. Also, the strain of the present invention has gastric juice tolerance and, when taken into a body of a human or animal, reaches the digestive (intestinal) tract alive with a high percentage to exert physiological functions. Accordingly, it is significantly useful in industry.

The invention claimed is:

1. A biologically pure culture of *Bifidobacterium longum* FERM BP-7787 having the following characteristics:
    (1) survival rate of 50% or higher, after attaining pH 4.4 to 4.6 in a milk base medium, and storing at 10° C. for two weeks; and
    (2) survival rate of 10% or higher in the case of storing in artificial gastric juice of pH 3.0 at 37° C. for two hours.

* * * * *